United States Patent
Stehr et al.

(10) Patent No.: US 7,328,071 B1
(45) Date of Patent: Feb. 5, 2008

(54) LEAD PLACEMENT DEVICE

(75) Inventors: Richard E. Stehr, Stillwater, MN (US); Daniel J. Potter, Stillwater, MN (US)

(73) Assignee: Pacesetter, Inc., Sylmar, CA (US)

( * ) Notice: Subject to any disclaimer, the term of this patent is extended or adjusted under 35 U.S.C. 154(b) by 99 days.

(21) Appl. No.: 11/249,968

(22) Filed: Oct. 12, 2005

(51) Int. Cl.
*A61B 19/00* (2006.01)

(52) U.S. Cl. ............... 607/131; 600/585; 606/129

(58) Field of Classification Search .......... 606/129, 606/108; 607/115–116, 119, 122–123, 129, 607/131; 600/372–374, 377, 585
See application file for complete search history.

(56) References Cited

U.S. PATENT DOCUMENTS

| | | | |
|---|---|---|---|
| 4,972,833 A | 11/1990 | Wildon | 128/419 P |
| 5,176,135 A | 1/1993 | Fain et al. | 128/419 P |
| 5,336,252 A | 8/1994 | Cohen | 607/119 |
| 5,545,207 A | 8/1996 | Smits et al. | 607/130 |
| 5,649,936 A * | 7/1997 | Real | 606/130 |
| 5,871,532 A | 2/1999 | Schroeppel | 607/128 |
| 6,231,518 B1 | 5/2001 | Grabek et al. | 600/508 |
| 6,266,567 B1 | 7/2001 | Ishikawa et al. | 607/36 |
| 2003/0074041 A1 | 4/2003 | Parry et al. | 607/130 |
| 2003/0114908 A1 | 6/2003 | Flach | 607/129 |
| 2003/0212446 A1 | 11/2003 | Kaplan et al. | 607/129 |
| 2005/0004644 A1* | 1/2005 | Kelsch et al. | 607/131 |

FOREIGN PATENT DOCUMENTS

| | | |
|---|---|---|
| EP | 1 321 165 A2 | 6/2003 |
| WO | WO 03/086502 A2 | 10/2003 |
| WO | WO 03/086502 A3 | 10/2003 |
| WO | WO 2004/002288 A2 | 1/2004 |
| WO | WO 2004/002288 A3 | 1/2004 |
| WO | WO 2004/011081 A1 | 2/2004 |

* cited by examiner

*Primary Examiner*—Kennedy J. Schaetzle

(57) ABSTRACT

Lead placement apparatus to transmit electrical signals to stimulate selected body tissue includes an introducer handle supporting a tubular outer sheath of flexible resilient material including a rigid section and a deflectable section adjacent the distal end, enabling the deflectable section to deflect among a plurality of positions in orientations transverse of a longitudinal axis. An operative member on the introducer handle connected to the distal end of the outer sheath serves to move that distal end. An inner tubular sheath of flexible resilient material slidably received within the outer sheath includes a driving socket fixed to its distal end whereby, with a lead slidably received within the inner tubular sheath and including a driven socket fixed to its distal end for releasable mating engagement by the driving socket, an electrode at the distal tip of the lead can be advanced and directed to the selected body tissue for stimulation.

18 Claims, 10 Drawing Sheets

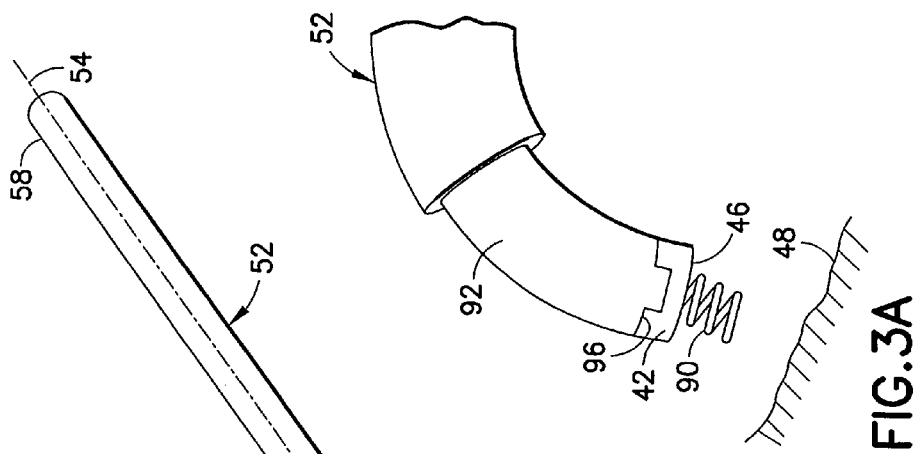
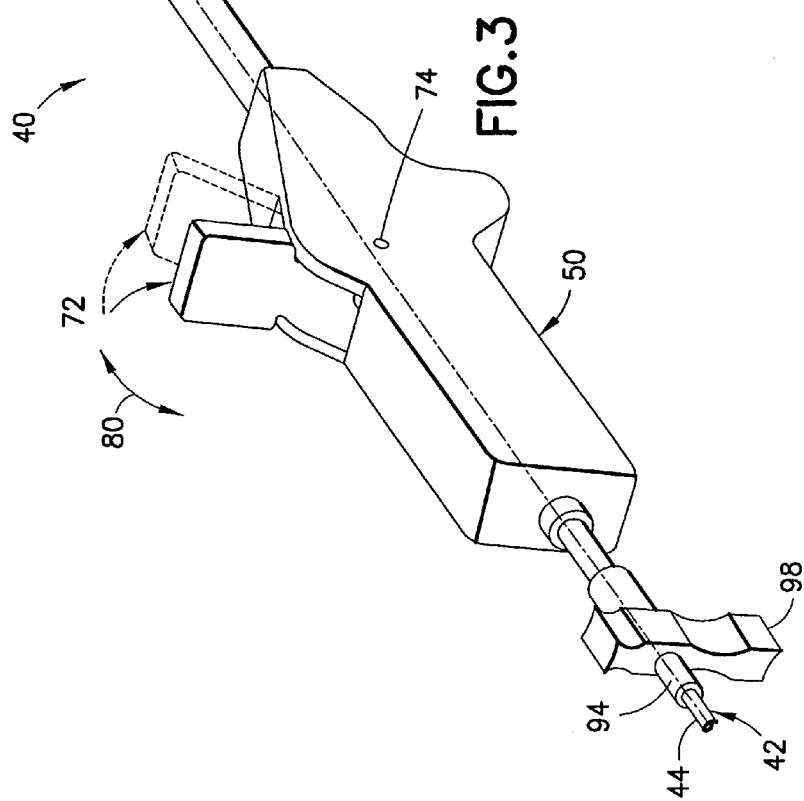

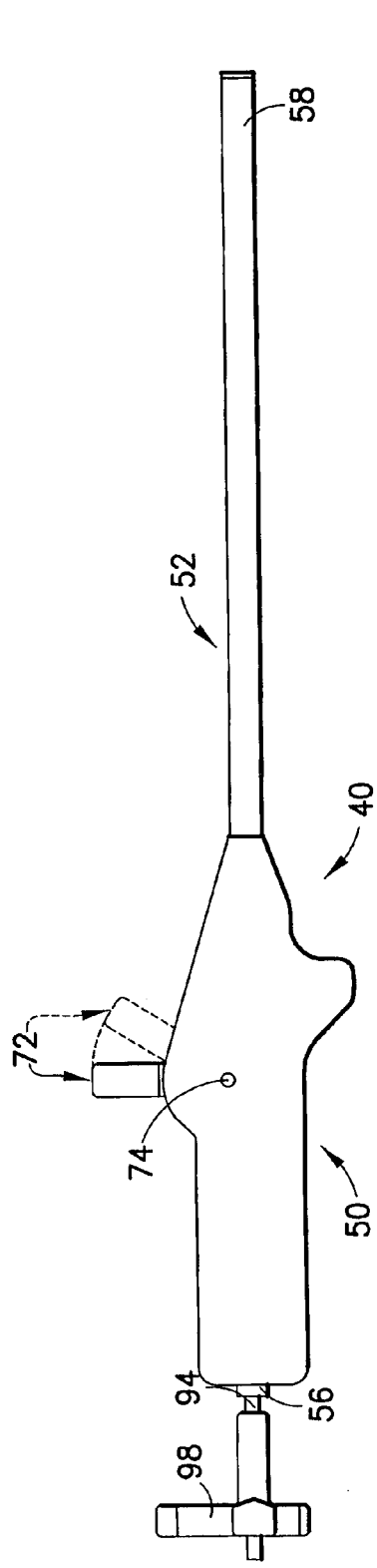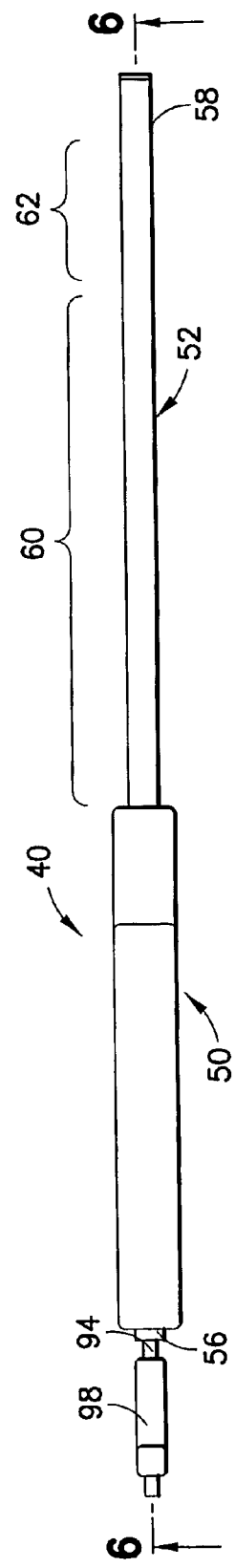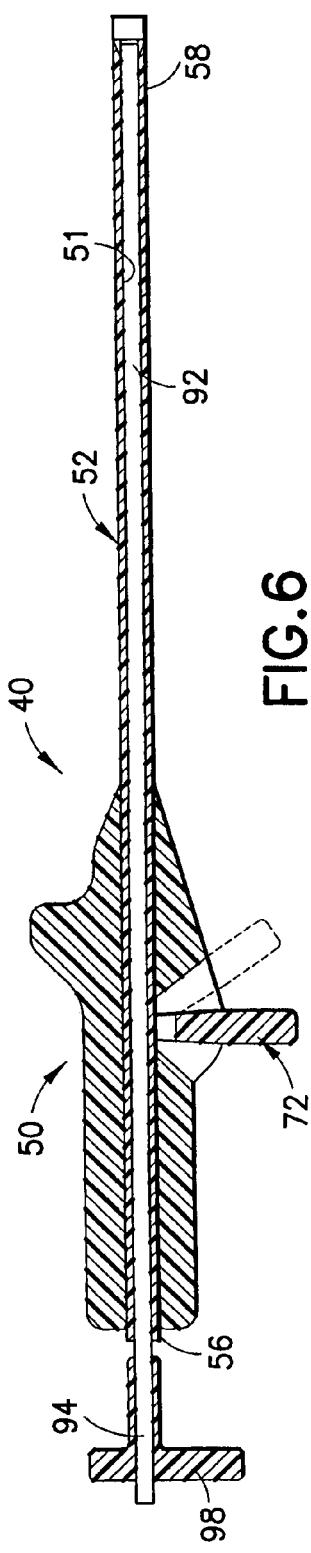

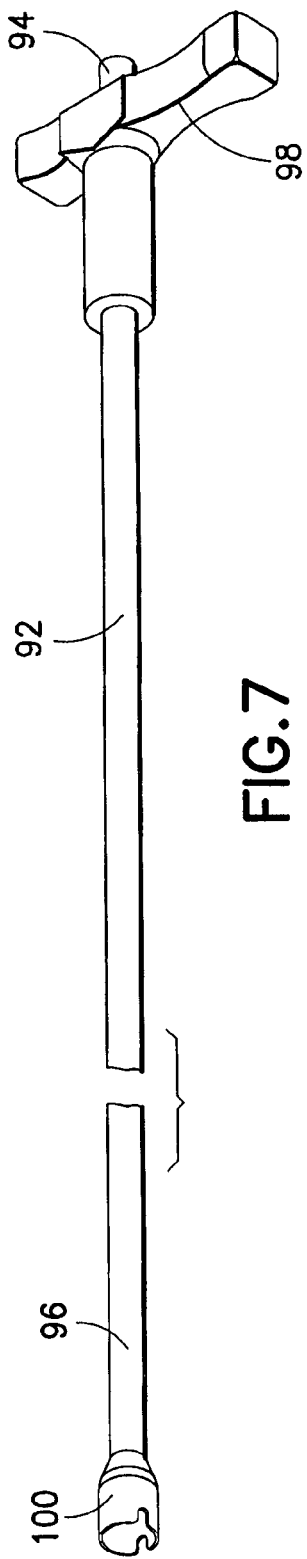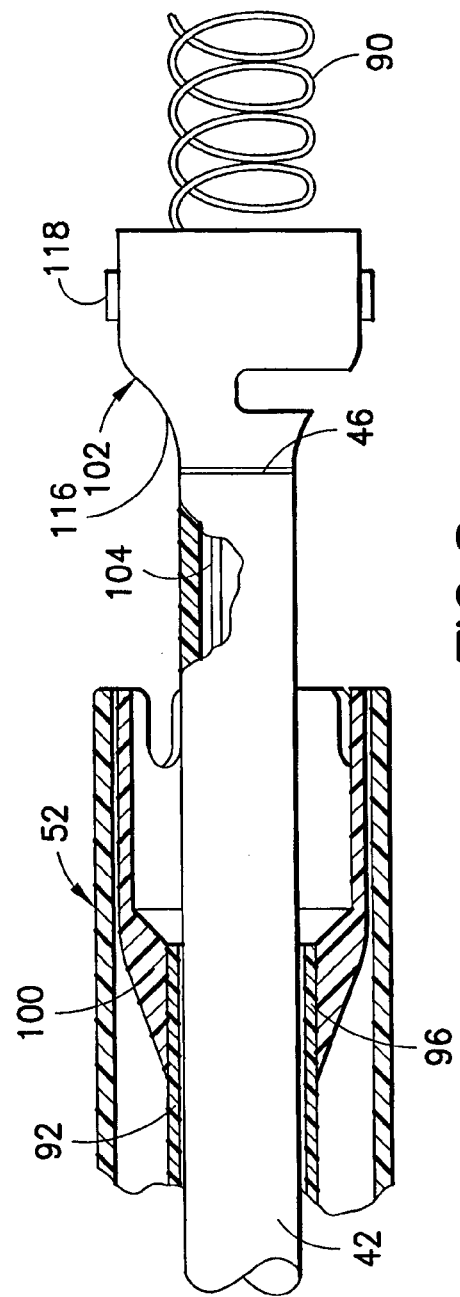

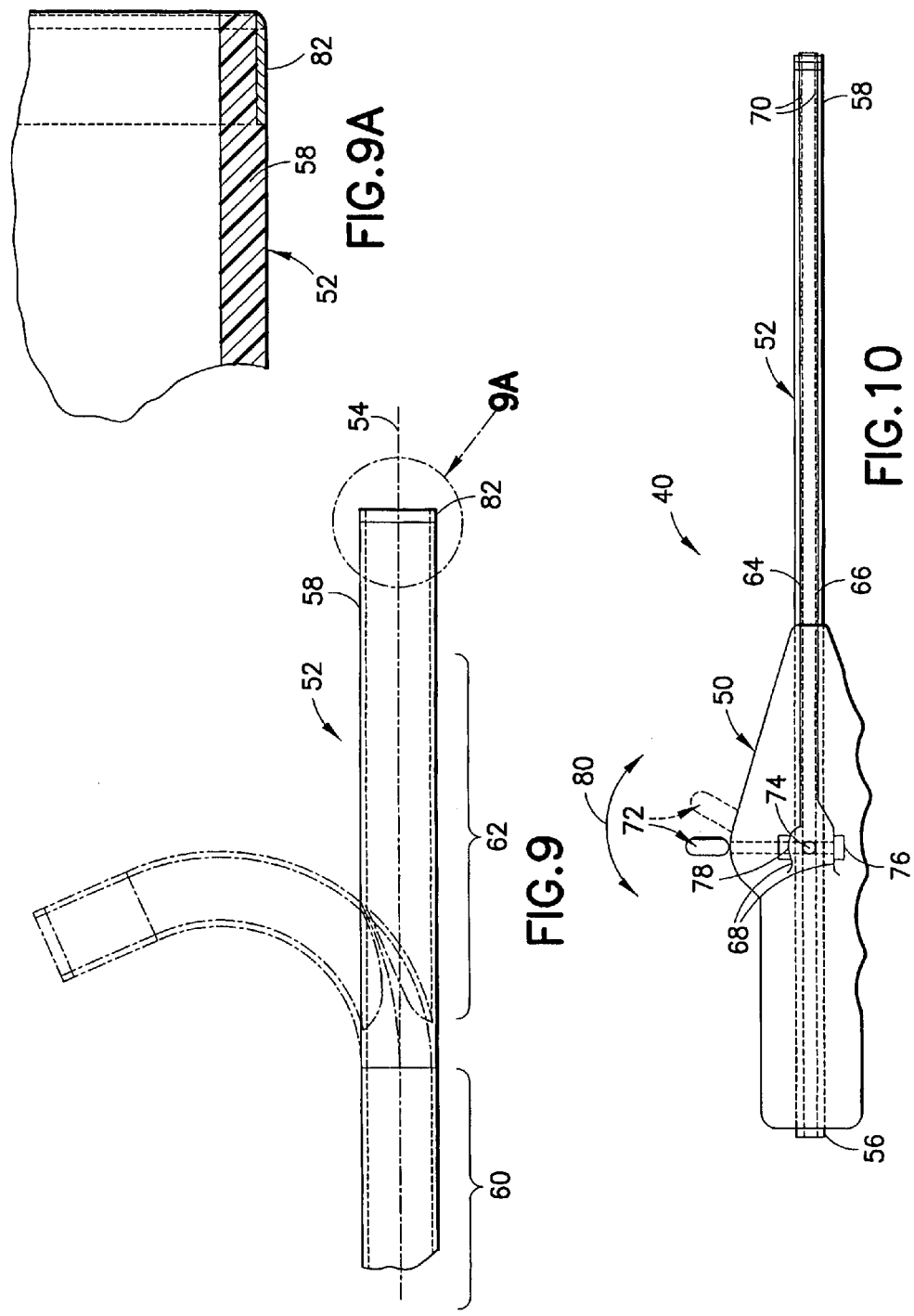

LEAD PLACEMENT DEVICE

FIELD OF THE INVENTION

The present invention relates generally to implantable medical devices for providing stimulating pulses to selected body tissue, and more particularly, to implantable cardiac stimulation leads of the epicardial type.

BACKGROUND OF THE INVENTION

Prior to the advent of endocardially implanted leads and associated surgical implantation techniques, surgeons and cardiologists traditionally relied on epicardial leads for cardiac stimulation and diagnosis. Median sternotomy or anterior thoracotomy were commonly used techniques to access the pericardium for epicardial lead implantation. Both techniques involve a significant incision and the post-operative issues associated with large incisions, such as recuperation time, pain, risk of infection, and cosmetic results.

Patients and practitioners alike favor the use of endocardial leads for cardiac stimulation in most circumstances. The benefits of transvenous implantation are many, including improved post-operative cosmetic appearance, faster wound healing, less post-operative pain, and improved flexibility in electrode placement. In addition, many areas of the myocardium that do not normally lend themselves to epicardial stimulation, such as the interventricular septum or the coronary sinus, may be readily paced endocardially.

Despite the advantages associated with endocardial implantation, epicardial cardiac stimulation is still medically indicated for many patients, particularly children. Although the various indications for epicardial lead fixation in pediatric patients are numerous, some common factors include small stature, congenital heart defects with residual or potential right to left shunting, or lack of venous access to the chamber requiring pacing.

Early designs for myocardial leads required relatively large screw-in electrodes that were intended for ventricular applications only. Follow-on prior art electrode designs utilized a stab-on electrode that was configured to be inserted into the atrial or the ventricular myocardium in a direction almost tangential to, and just under, the epicardial surface. After the stab-on step, the electrode body was then sutured to the epicardial surface for stabilization. These prior art electrodes were most commonly implanted via median sternotomy or anterior thoracotomy The advent of thoracoscopy in cardiac surgery has shown promise as a technique to enable surgeons to implant epicardial leads without sternotomy or thoracotomy. Thoracoscopy normally involves penetration of the chest cavity with two or more tubular introducers that are passed through small incisions in the chest wall. Illumination devices, cutting instruments, sutures, and the like may be inserted into the chest cavity via the introducers.

Despite the promise of thoracoscopy, many conventional epicardial leads utilize a widened suture pad that is normally disk-shaped and includes one or more suture holes for guiding a suture needle into the epicardium. These disk-like suture pads may present the surgeon with certain difficulties during insertion via a typical thoracoscopy introducer. To begin with, there is the potential for the suture pad to resist movement through the introducer. Unless extreme caution is exercised, the lead may be damaged. To avoid the potential for snagging the lead, surgeons may have to use a larger than necessary introducer, resulting in a larger incision, more scarring, and potentially more post-operative pain for the patient. In addition, if a conventional suture pad epicardial lead must be relocated due to improper threshold or some other indication, the surgeon must expend time and effort cutting the existing sutures and sewing the pad to the new location.

Another solution proposed for myocardial lead implantation utilizes a sutureless screw-in electrode. The electrode is screwed into the myocardium perpendicular to the surface of the epicardium while the lead is laid approximately parallel to the epicardium surface. The arrangement produces an almost 90 degree bend in the lead just proximal to the electrode that may give rise to forces capable of dislodging the electrode and/or injuring the epicardium, particularly in view of the normally vigorous cyclic movement of the epicardium. Injury to the epicardium may also occur if the rib cage is compressed against the 90 degree bend during rough play or other exercise.

Another existing lead design incorporates a projectable side hook that is normally biased in a retracted position by a coil spring. The side hook is moved to an extended position by application of axial force from a stylet to an internally disposed leg of the side hook that includes a roller disposed in an arcuate channel. The fabrication of this system requires a series of complex molding and machining steps, often under relatively tight tolerances. In operation, this system relies on a series of cooperating rollers, curved slots, and springs that may be subject to malfunction during implantation, and requires the surgeon to simultaneously apply axial force on a stylet and torsional force on the lead.

It was in light of the foregoing that the present invention was conceived and has now been reduced to practice.

SUMMARY

According to the invention, lead placement apparatus to transmit electrical signals to stimulate selected body tissue includes an introducer handle supporting a tubular outer sheath of flexible resilient material including a rigid section and a deflectable section adjacent the distal end, enabling the deflectable section to deflect among a plurality of positions in orientations transverse of a longitudinal axis. An operative member on the introducer handle connected to the distal end of the outer sheath serves to move that distal end. An inner tubular sheath of flexible resilient material slidably received within the outer sheath includes a driving socket fixed to its distal end whereby, with a lead slidably received within the inner tubular sheath and including a driven socket fixed to its distal end for releasable mating engagement by the driving socket, an electrode at the distal tip of the lead can be advanced and directed to the selected body tissue for stimulation.

The invention, then, is a two-piece steerable introducer that facilitates the placement and attachment of a pacing lead to the exterior of the heart. The exterior sheath provides the steering motion while the inner sheath holds the leads and allows the user to rotate the lead to attach a helical coil such as those found on most positive fixation leads. This is in contrast to current practice which uses a single steerable sheath using a stylet or other internal drivers that severely limit the torque available to fasten the lead.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 3 is a perspective view of one embodiment of lead placement apparatus in accordance with the invention;

FIG. 3A is a detail perspective of a distal end of a lead used with the invention to stimulate selected body tissue 48;

FIG. 4 is a side elevation view of the lead placement apparatus illustrated in FIG. 3;

FIG. 5 is a bottom plan view of the lead placement apparatus illustrated in FIG. 3;

FIG. 6 is a cross section view taken generally along 6-6 in FIG. 5;

FIG. 7 is a perspective view of a component of the lead placement apparatus illustrated in FIG. 6;

FIG. 8 is a detail side elevation view, partly cut away and in section, of components which are part of the lead placement apparatus of the invention;

FIG. 9 is a detail side elevation view of the distal end of a component illustrated in FIGS. 3-6 and illustrating two different positions of which it is capable;

FIG. 9A is a detail cross section view of the distal end of the component illustrated in FIG. 9;

FIG. 10 is a side elevation view in section generally similar to FIG. 6 to illustrate one embodiment for operating the apparatus;

DETAILED DESCRIPTION

Figure 1:
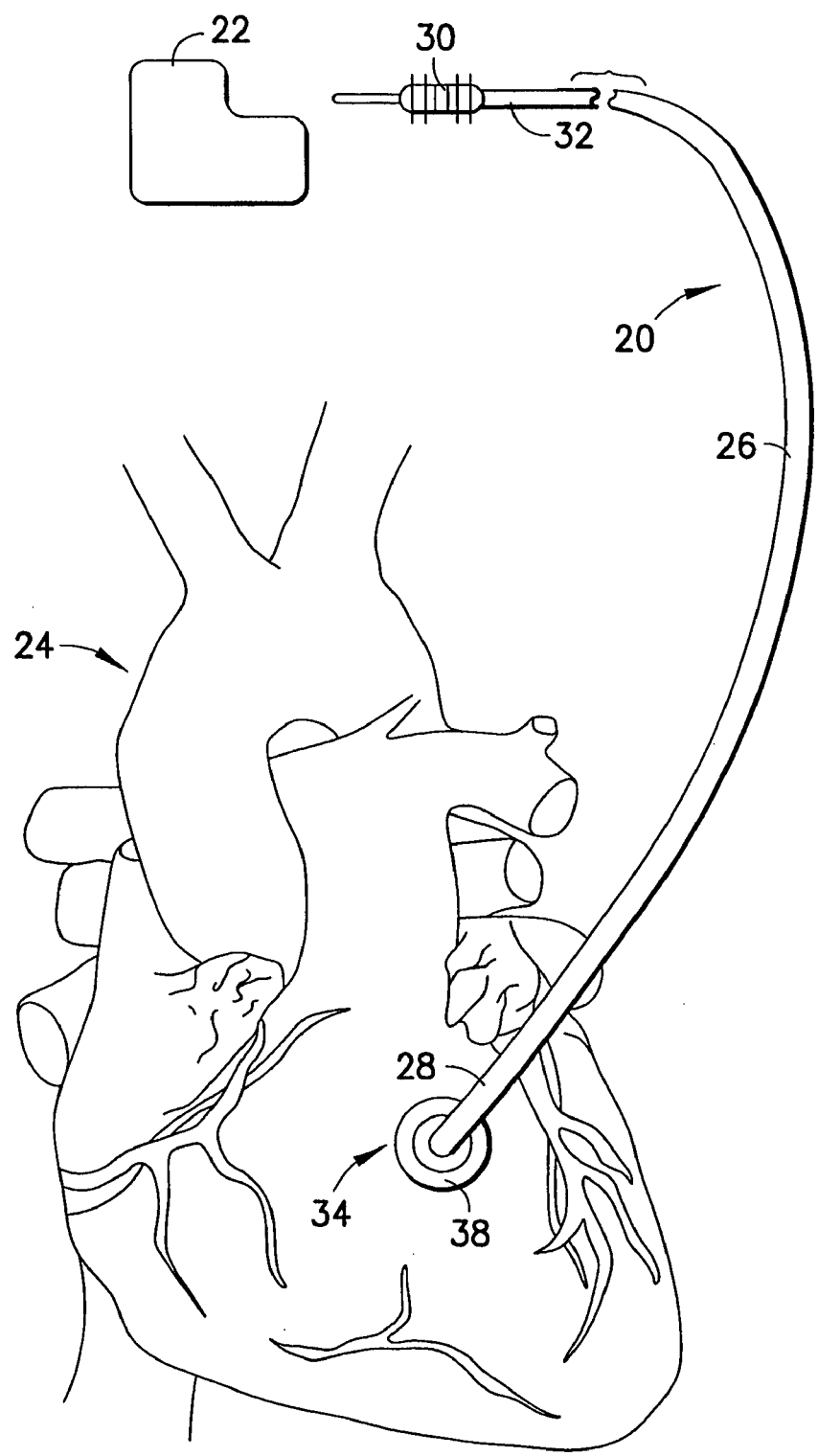
FIG. 1 is a diagrammatic perspective view illustrating an implanted lead system for providing electrical stimulation of a heart employing an implanted lead embodying the present invention.
Figure 2:
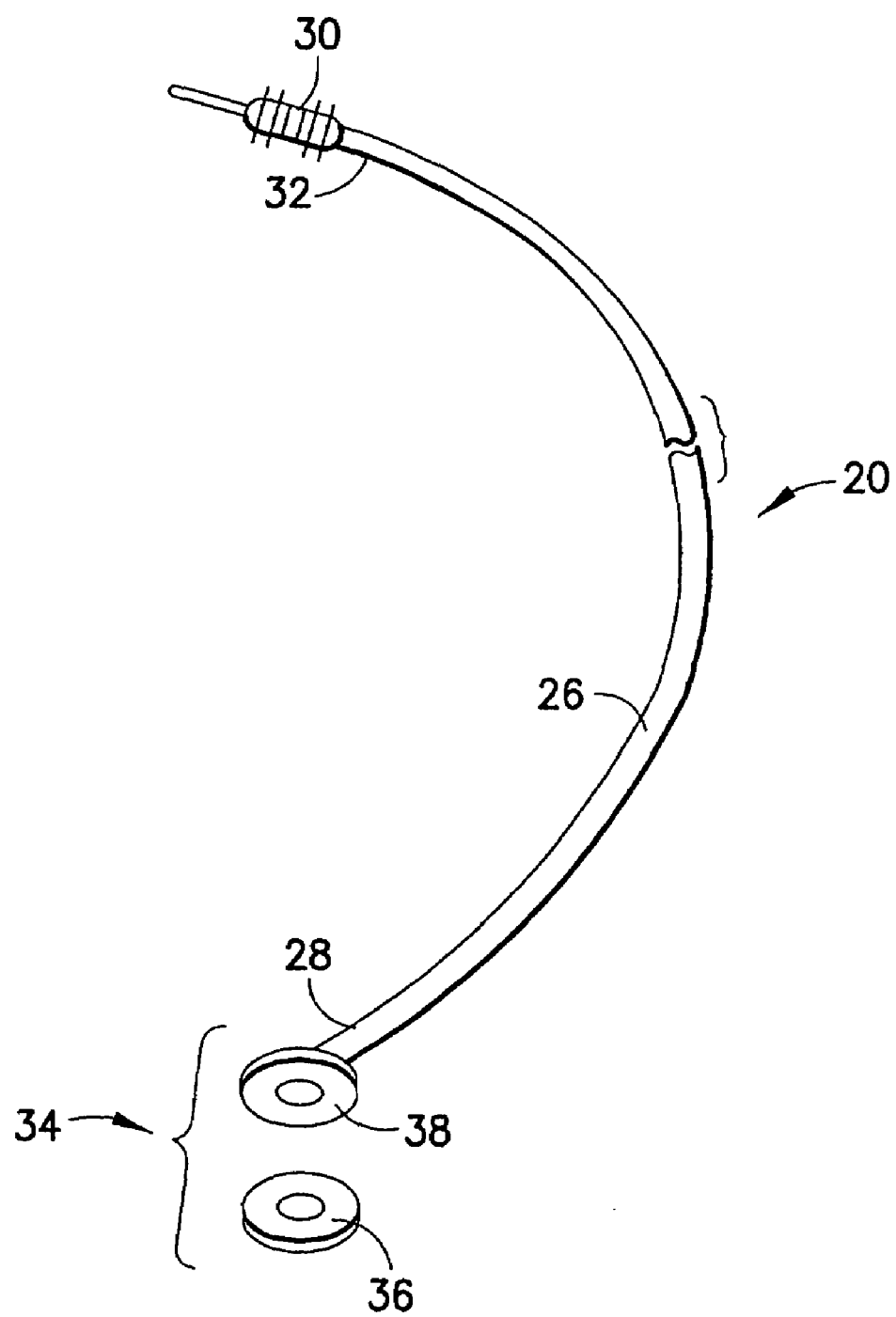
FIG. 2 is an exploded perspective view of the lead illustrated in FIG. 1 in a detached condition.

Refer now to the drawings and, initially, to FIGS. 1 and 2 in which are shown diagrammatic perspective views of a medical electrical, epicardial or myocardial lead 20 of a known design but which may be modified to incorporate features of the present invention for use in association with an electrical stimulator 22 such as a pacemaker or defibrillator providing electrical stimulation to a heart 24. Although the present invention will be described with reference to the embodiments shown in the drawings, it should be understood that the present invention can be embodied in many alternate forms or embodiments. In addition, any suitable size, shape or type of elements or materials could be used.

The lead 20 is adapted to conduct electrical stimulation from the electrical stimulator 22, which may be, alternatively and selectively, implantable or external to a site of the heart 24 and to conduct electrical signals of the heart from the site to the stimulator. The lead 20 includes an elongated lead body 26 extending from a lead body distal end 28 to a connector 30 at the lead body proximal end 32 for mechanical and electrical attachment to the electrical stimulator 22. An electrode head 34 is provided at the lead body distal end 28 and includes an electrode tip member 36 (FIG. 2) adapted to be fixated to the heart and an electrode backing member 38 fixed to the distal end 28 of the lead body 26 and releasably attachable to the electrode tip member. When the electrode tip member 36 and the electrode backing member 38 are attached, electrical signals can be transmitted between the heart 24 and the electrical stimulator 22.

The present invention can be employed to assist positioning of the distal end 28 of the lead 20 so the electrode backing member 38 can be attached to the electrode tip member. However, in describing the present invention, as seen now in FIGS. 3, 4, 5, 6, 7, and 8, lead placement apparatus 40 will be primarily directed to the positioning of a positive fixation lead 42. In the manner of the lead 20 as illustrated in FIG. 1, the lead 42 extends between a body implantable stimulating pulse generator (not shown in this instance) adapted to transmit electrical signals between a proximal end portion 44 of the lead and a distal end 46 to stimulate selected body tissue 48 (FIG. 3A). In a first embodiment of the invention, the apparatus 40 includes an introducer handle 50 with a longitudinally extending bore 51 and an elongated tubular outer sheath 52 of flexible resilient material extending through the bore and fixed in any suitable manner to the introducer handle generally aligned with a longitudinal axis 54 of the introducer handle and extending between proximal and distal ends 56, respectively. The outer sheath 52 may be of braided (metallic or polymeric braiding wire) or non-braided polyurethane, pebax, polyethylene or other suitable biocompatible plastic material of sufficient kink resistance and flexibility and has a rigid section 60 (FIGS. 5 and 9) distant from the distal end 58 and a deflectable section 62 adjacent the distal end. This construction enables the deflectable section 62 to deflect from a first solid line position aligned with the longitudinal axis 54 to a plurality of second positions in orientations transverse of the longitudinal axis, one such second position being indicated by dashed lines in FIG. 9.

Figure 11:
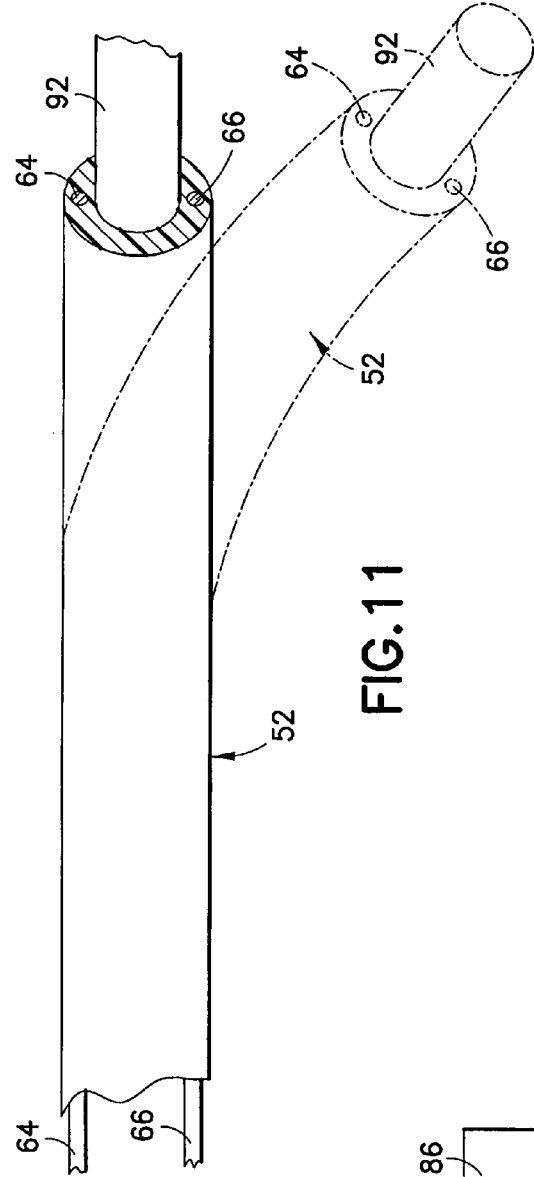
FIG. 11 is a detail elevation view, partly in section, to illustrate in more detail components for operating the apparatus.

A pair of elongated steering members 64, 66, of stainless steel wire, for example, are embedded in the outer sheath 52. Viewing now FIGS. 10 and 11, each steering member 64, 66 extends between a proximal end 68 at the introducer handle 50 and a distal end 70 at the distal end 58 of the outer sheath 52. As seen now in FIGS. 3, 4, 6, and 10, an operative member in the form of a lever 72 is mounted on the introducer handle 50 for movement about a pivot axis 74 between a first solid line position and any one of a plurality of second positions, one such second position being indicated by dashed lines in each figure. As will be explained shortly, when the lever 72 is in the first solid line position, the distal end 58 of the outer sheath 52 is in the first position mentioned earlier and when the lever 72 is in one of the plurality of second dashed line positions, the distal end of the outer sheath is similarly in an associated one of the plurality of the second positions.

More specifically, as seen especially well in FIG. 10, the lever 72 includes a first free end 76 for manual operation spaced in one direction spaced radially away from the pivot axis 74 to which the proximal end 68 of the steering member 64 is attached. Similarly, a second end 78 of the lever 72 is spaced in an opposite direction spaced radially away from the pivot axis 74 and is attached to the proximal end 68 of the steering member 66. With this construction, then, it can be seen that pivotal movement of the lever 72 on the pivot axis 74 in the directions indicated by an arcuate double headed arrow 80 (FIGS. 3 and 10) is effective to move the distal end 58 of the outer sheath from the first solid line position to any of the plurality of second, dashed line, positions. It can also be said, therefore, that the proximal ends 68 of the steering members 64, 66 are fixed, respectively, to the lever 72 at diametrically opposed locations away from the pivot axis 74.

It will be appreciated that although a pair of the steering members 64 and 66 have been shown and described, a single steering member could be effective to achieve the desired movement of the distal end 58 of the outer sheath 52 and it is also within the realm of the invention for plural steering members, that is, in excess of two, to be used.

Figure 12:
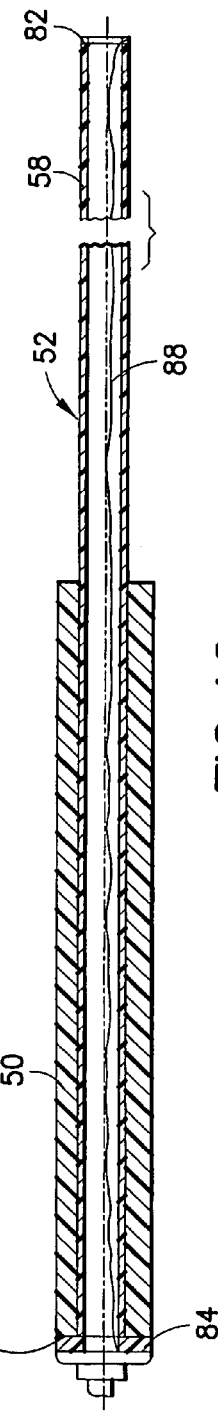
FIG. 12 is a detail elevation view, in cross section, of components which are used in combination with the structure illustrated in FIGS. 9 and 9A.

Turning now to FIGS. 9, 9A, and 12, a ring electrode 82 is seen placed at the distal end 58 of the outer sheath 52, an electrode port 84 is positioned on the introducer handle 50 for connection to an electrical mapping system 86, and an electrode wire 88 extends through the outer sheath connecting the ring electrode to the electrode port. With this construction, the electrode port 84 can be directed in a manner yet to be described to find a desirable site for placement of a helical tip electrode 90 of the lead 46 for stimulating the body tissue 48.

As seen especially well in FIG. 8, an inner tubular sheath 92 of braided (metallic or polymeric braiding wire) or non-braided polyurethane, pebax, polyethylene or other suitable biocompatible plastic material of sufficient kink resistance and flexibility is slidably received within the outer sheath 52 extending between proximal and distal ends 94, 96, respectively. A knob 98 is fixed to the proximal end 94 of the inner sheath 92 (FIGS. 3-7). A driving socket 100 is fixed to the distal end 96 of the inner sheath 92 and the lead 42 for a stimulating pulse generator having the nature of the component 22 in FIG. 1 extends between proximal and distal ends 94, 96 and is slidably received within the inner tubular sheath 92.

A driven socket 102 is fixed to the distal end 46 of the lead 42 for connection to its associated stimulating pulse generator and positioned for releasable mating engagement by the driving socket 100 so that the tip electrode 90 for the lead can be advanced to the body tissue 48 for its selective stimulation. In a known manner, an electrical conductor 104 extending between the proximal end 44 and the distal end 46 is received within the lead 42 for the stimulating pulse generator. An electrical connector like connector 30 in FIG. 1 is coupled to the proximal end of the electrical conductor 104 for releasable attachment to a stimulating pulse generator like the stimulating pulse generator 22 of FIG. 1 and thereby connects to the tip electrode 90 at the distal end of the electrical conductor. As noted earlier, the lead 42 is a positive fixation lead such that the tip electrode 90 is a fixing helix electrode for engaging the selected body tissue.

Figure 13:
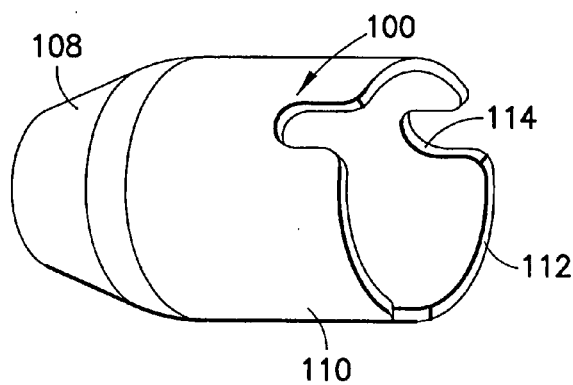
FIG. 13 is a perspective view of a driving socket used by the apparatus of the invention.
Figure 14:
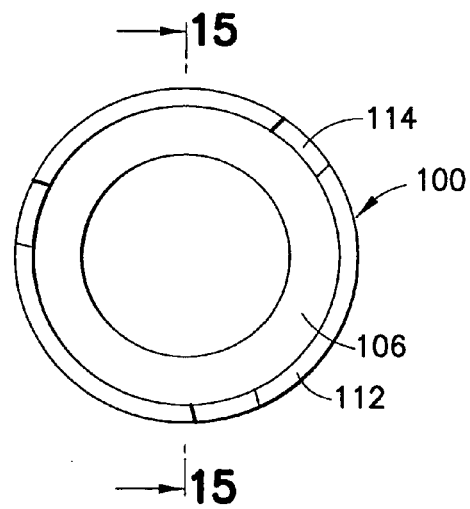
FIG. 14 is an end elevation view of the driving socket illustrated in FIG. 13.
Figure 15:
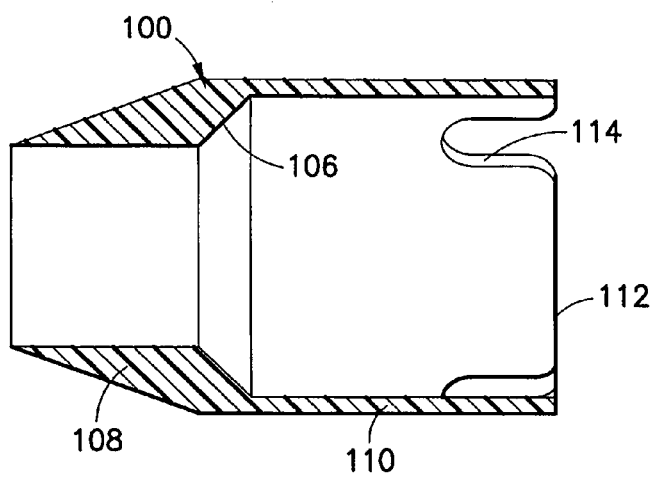
FIG. 15 is a cross section view taken generally along 15-15 in FIG. 14.
Figure 17:
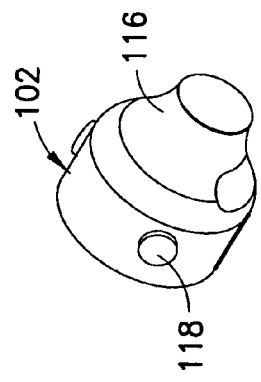
FIGS. 16 and 17 are perspective views illustrating different orientations of a driven socket used by the apparatus of the invention.
Figure 16:
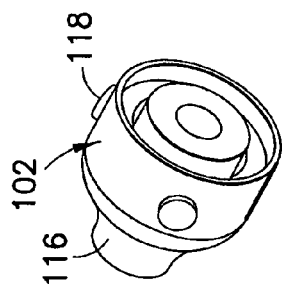
Figure 20:
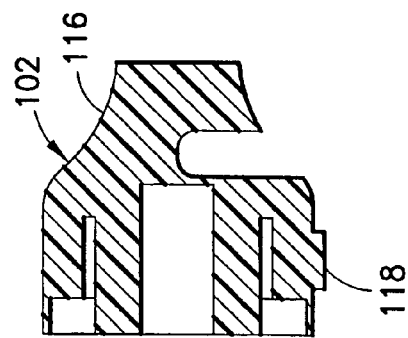
FIG. 20 is a cross section view taken generally along 19-19 in FIG. 18.
Figure 19:
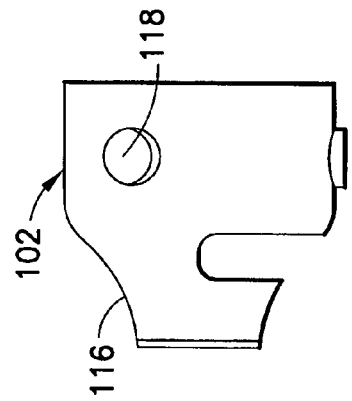
FIG. 19 is a side elevation view of the driven socket illustrated in FIGS. 16, 17 and 18.
Figure 18:
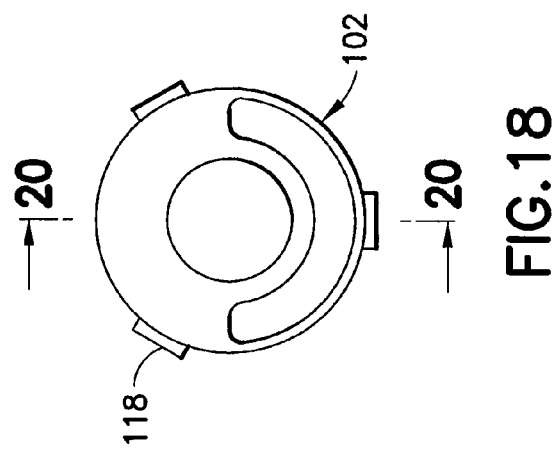
FIG. 18 is an end elevation view of the driven socket illustrated in FIGS. 16 and 17.

For purposes of the invention and in a manner to be described, the driving socket 100 (FIGS. 13, 14, and 15 for greater detail) and the driven socket 102 (FIGS. 16-20 for greater detail) include mutually engageable mating features. The driving socket 100 has a concave distal end region 106 and, generally, as seen in FIGS. 13 and 15, is cup shaped and includes a base member 108 with a bore 110 for fitting engagement on the distal end 96 of the inner sheath 92 and an outstanding cylindrical wall 110 extending distally to a rim 112 with circumferentially spaced cutouts 114. The driven socket 102 is generally cylindrical, has a convex proximal end region 116 matingly engageable with the driving socket 100, and includes a plurality of circumferentially spaced outwardly projecting boss members 118. The circumferentially spaced cutouts 114 of the driving socket 100 are slidably matingly engageable with the boss members 118 of the driven socket 102 for advancing the distal end 46 of the lead 42 for the stimulating pulse generator to a selected body tissue location.

With this construction, using the introducer handle 50, the outer sheath 52 is advanced and a desirable tissue site sought and located using the lever 72 to move the distal end 58 and its ring electrode 82 connected to the electrical mapping system 86. When the desired tissue site is located, the driving socket 100 and the driven socket 102 are engaged, and with the knob 98, the driving socket is operable for advancing the distal end 46 of the lead 42 for the stimulating pulse generator to the selected body tissue location. Then the knob is rotated and, with it, the fixing helix tip electrode 90 for engaging the selected body tissue.

Figure 21:
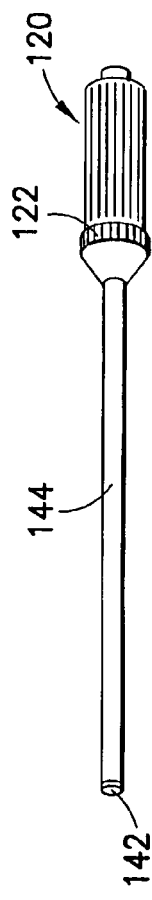
FIG. 21 is a perspective view of another embodiment of lead placement apparatus in accordance with the invention.
Figure 22:
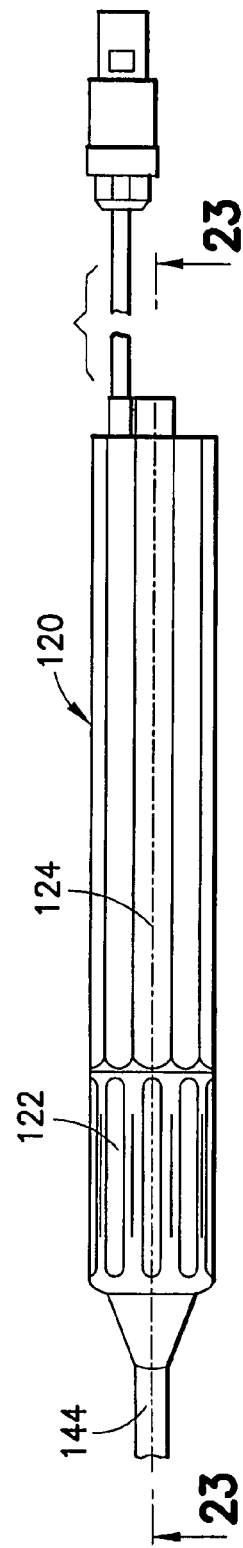
FIG. 22 is a side elevation view of the lead placement apparatus illustrated in FIG. 21.
Figure 23:
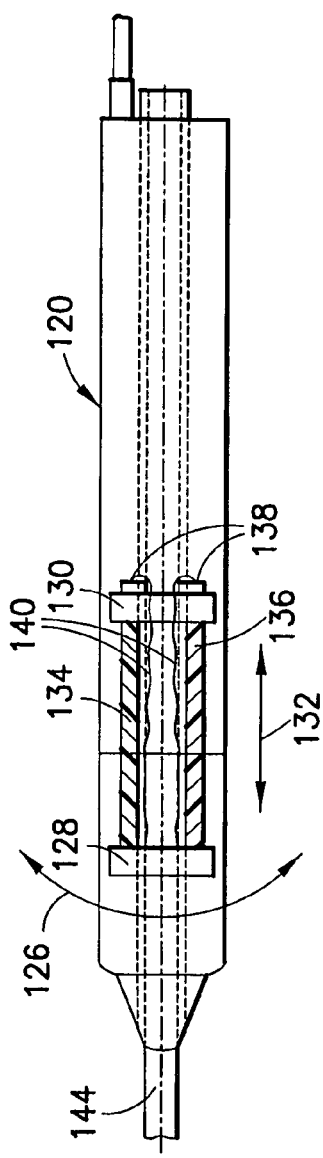
FIG. 23 is a cross section view taken generally along 23-23 in FIG. 22.

In another, and preferred, instance, viewing FIGS. 21, 22, and 23, an operative member for an introducer handle 120 is a dial member 122 rotatably mounted for rotation about a longitudinal axis generally parallel with a longitudinal axis 124 of the introducer handle. As in the instance of the lever 72, the dial member is set for movement between a first position and any one of a plurality of second positions. As the dial member 122 is rotated about axis 124 in either of the directions indicated by a double arcuate arrowhead 126, thread blocks 128, 130 are moved in a linear fashion as indicated by double arrowhead 132. This results because of mating threaded drive blocks 134, 136 which are threadedly engaged with the thread blocks. A wire attachment block 138 serves to fasten each of one or more elongated steering members 140 at their proximal ends, their distal ends being attached to a distal end 142 of an outer sheath 144 to which the introducer handle 120 is mounted.

Thus, with rotation of the of the dial member 122 in either direction about the longitudinal axis 124, and in the manner of the earlier described embodiment, the distal end 142 of the outer sheath 144 is moved from first position to a plurality of second positions.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An implantable lead assembly comprising:
an introducer handle having a longitudinal axis;
an elongated tubular outer sheath of flexible resilient material having a longitudinal axis fixed to the introducer handle generally aligned with the longitudinal axis thereof and extending between proximal and distal ends, the outer sheath having a rigid section distant from the distal end and a deflectable section adjacent the distal end, enabling the deflectable section adjacent the distal end to deflect from a first position aligned with the longitudinal axis to a plurality of second positions in orientations transverse of the longitudinal axis;
at least one elongated steering member embedded in the outer sheath and extending between a proximal end at the introducer handle and a distal end at the distal end of the outer sheath;
an operative member mounted on the introducer handle for movement between a first position and any one of a plurality of second positions, the operative member attached to the proximal end of the steering member such that when in the first position, the distal end of the outer sheath is in the first position and when in one of the plurality of second positions, the distal end of the outer sheath is in an associated one of the plurality of the second positions;
an inner tubular sheath of flexible resilient material slidably received within the outer sheath extending between proximal and distal ends;
a knob fixed to the proximal end of the inner sheath;
a driving socket fixed to the distal end of the inner sheath;
a lead extending between proximal and distal ends slidably received within the inner tubular sheath, the lead having a helix tip electrode at the distal end; and
a driven socket fixed to the distal end of the lead and positioned for releasable mating engagement by the driving socket;
wherein with engagement of the driven socket by the driving socket and movement of the knob and inner sheath in the distal direction, the helix tip electrode for the lead can be advanced to the selected body tissue for stimulation thereof; and
wherein rotation of the knob rotates the inner sheath, the driving socket, and the driven socket such that the helix tip electrode rotatable engages with the selected body tissue.

2. An implantable lead assembly as set forth in claim 1 wherein the lead includes:
an electrical conductor received within the lead for the stimulating pulse generator extending between a proximal end and a distal end;
an electrical connector coupled to the proximal end of the electrical conductor for releasable attachment to a stimulating pulse generator; and
an electrode coupled to the distal end of the electrical conductor.

3. An implantable lead assembly as set forth in claim 1 wherein the outer sheath includes a pair of diametrically opposed steering members embedded in the outer sheath; and
wherein the operative member is attached to the proximal ends of the steering members such that when in the first position, the distal end of the outer sheath is in the first position and when in the plurality of second positions, the distal end of the outer sheath is in the associated plurality of second positions.

4. An implantable lead assembly as set forth in claim 1 wherein the introducer handle has a longitudinally extending bore; and
wherein the outer sheath extends through the bore of the introducer handle.

5. An implantable lead assembly as set forth in claim 1 including:
a ring electrode at the distal end of the outer sheath;
an electrode port on the introducer handle for connection to an electrical mapping system; and
a wire lead extending through the outer sheath connecting the ring electrode to the electrode port.

6. An implantable lead assembly as set forth in claim 1 wherein the driving socket and driven socket include mutually engageable mating features.

7. An implantable lead assembly as set forth in claim 1 wherein the driving socket has a concave distal end region;
wherein the driven socket has a convex proximal end region matingly engageable with the driving socket; and
wherein, when the driving socket and the driven socket are engaged, the driving socket is operable for advancing the distal end of the lead for the stimulating pulse generator to a selected body tissue location.

8. An implantable lead assembly as set forth in claim 1 wherein the lead is a positive fixation lead.

9. An implantable lead assembly as set forth in claim 1 wherein the driving socket is cup shaped including:
a base member with a bore for fitting engagement on the distal end of the inner sheath; and
an outstanding cylindrical wall extending distally to a rim with circumferentially spaced cutouts; and
wherein the driven socket is generally cylindrical including:
a plurality of circumferentially spaced outwardly projecting boss members;
wherein the circumferentially spaced cutouts of the driving socket are slidably matingly engageable with the boss members of the driven socket for advancing the distal end of the lead for the stimulating pulse generator to a selected body tissue location.

10. Lead placement apparatus for positioning the lead of a body implantable stimulating pulse generator adapted to transmit electrical signals between a proximal end portion of the lead and a distal end portion thereof to thereby stimulate selected body tissue comprising:
an introducer handle having a longitudinal axis;
an elongated tubular outer sheath of flexible resilient material having a longitudinal axis fixed to the introducer handle generally aligned with the longitudinal axis thereof and extending between proximal and distal ends, the outer sheath having a rigid section distant from the distal end and a deflectable section adjacent the distal end, enabling the deflectable section adjacent the distal end to deflect from a first position aligned with the longitudinal axis to a plurality of second positions in orientations transverse of the longitudinal axis;
at least one elongated steering member embedded in the outer sheath and extending between a proximal end at the introducer handle and a distal end at the distal end of the outer sheath;
an operative member mounted on the introducer handle for movement between a first position and any one of a plurality of second positions, the operative member attached to the proximal end of the steering member such that when in the first position, the distal end of the outer sheath is in the first position and when in one of the plurality of the second positions, the distal end of the outer sheath is in an associated one of the plurality of the second positions;

an inner tubular sheath of flexible resilient material slidably received within the outer sheath extending between proximal and distal ends;

a knob fixed to the proximal end of the inner sheath; and a driving socket fixed to the distal end of the inner sheath;

wherein, with a lead for the stimulating pulse generator extending between proximal and distal ends slidably received within the inner tubular sheath and including a driven socket fixed to the distal end thereof for releasable mating engagement by the driving socket, with engagement of the driven socket by the driving socket and movement of the knob and inner sheath in the distal direction, a helix tip electrode at the distal tip of the lead can be advanced to the selected body tissue for stimulation thereof; and wherein rotation of the knob rotates the inner tubular sheath, the driving socket, and the driven socket such that the helix tip electrode engages with the selected body tissue.

11. A lead placement apparatus as set forth in claim 10 wherein the outer sheath includes a pair of diametrically opposed steering members embedded in the outer sheath; and wherein the operative member is attached to the proximal ends of the steering members such that when in the first position, the distal end of the outer sheath is in the first position and when in the plurality of second positions, the distal end of the outer sheath is in the associated plurality of second positions.

12. A lead placement apparatus as set forth in claim 10 wherein the introducer handle has a longitudinally extending bore; and wherein the outer sheath extends through the bore of the introducer handle.

13. A lead placement apparatus as set forth in claim 10 wherein the operative member is a lever pivotally mounted on the introducer handle for rotation about a pivot axis including a first free end for manual operation spaced in one direction away from the pivot axis and a second end spaced in an opposite direction away from the pivot axis and attached to the proximal end of the steering member; and wherein pivotal movement of the lever about the pivot axis moves the distal end of the outer sheath from the first position to the plurality of second positions.

14. A lead placement apparatus as set forth in claim 10 wherein the operative member is a lever pivotally mounted on the introducer handle for rotation about a pivot axis including a first free end for manual operation spaced in one direction away from the pivot axis; and wherein the proximal end of the steering member is fixed to the lever at a location radially spaced from the pivot axis.

15. A lead placement apparatus as set forth in claim 10 including:

a ring electrode at the distal end of the outer sheath;

an electrode port on the introducer handle for connection to an electrical mapping system; and a wire lead extending through the outer sheath connecting the ring electrode to the electrode port.

16. A lead placement apparatus as set forth in claim 10 wherein the driving socket and driven socket include mutually engageable mating features.

17. A lead placement apparatus as set forth in claim 10 wherein the driving socket has a concave distal end region;

wherein the driven socket has a convex proximal end region matingly engageable with the driving socket; and wherein, when the driving socket and the driven socket are engaged, the driving socket is operable for advancing the distal end of the lead for the stimulating pulse generator to a selected body tissue location.

18. A lead placement apparatus as set forth in claim 10 wherein the driving socket is cup shaped including:

a base member with a bore for fitting engagement on the distal end of the inner sheath; and an outstanding cylindrical wall extending distally to a rim with circumferentially spaced cutouts; and wherein the driven socket is generally cylindrical including:

a plurality of circumferentially spaced outwardly projecting boss members;

wherein the circumferentially spaced cutouts of the driving socket are slidably matingly engageable with the boss members of the driven socket for advancing the distal end of the lead for the stimulating pulse generator to a selected body tissue location.

* * * * *